United States Patent
Fontana et al.

(10) Patent No.: US 8,742,118 B2
(45) Date of Patent: Jun. 3, 2014

(54) METHODS FOR PREPARING INTERMEDIATES OF PERAMPANEL

(71) Applicant: F.I.S.—Fabbrica Italiana Sintetici S.p.A., Alte di Montecchio Maggiore (IT)

(72) Inventors: Francesco Fontana, Como (IT); Paolo Stabile, Verona (IT)

(73) Assignee: F.I.S.—Fabbrica Italiana Sintetici S.p.A., Alte di Montecchio Maggiore (VI) (IT)

( * ) Notice: Subject to any disclaimer, the term of this patent is extended or adjusted under 35 U.S.C. 154(b) by 0 days.

(21) Appl. No.: 13/654,437

(22) Filed: Oct. 18, 2012

(65) Prior Publication Data

US 2013/0109862 A1    May 2, 2013

(30) Foreign Application Priority Data

Oct. 27, 2011   (IT) .............................. MI2011A1952

(51) Int. Cl.
*C07D 213/22*    (2006.01)
*A61K 31/44*     (2006.01)

(52) U.S. Cl.
USPC ........................................ 546/260; 514/340

(58) Field of Classification Search
None
See application file for complete search history.

(56) References Cited

U.S. PATENT DOCUMENTS

| | | |
|---|---|---|
| 2006/0004205 A1 | 1/2006 | Koyakumaru et al. |
| 2010/0016603 A1 | 1/2010 | Sonoda et al. |

FOREIGN PATENT DOCUMENTS

| | | |
|---|---|---|
| WO | 2011031754 A1 | 3/2011 |

OTHER PUBLICATIONS

Lutz Ackermann, Harish K.Rotukuchi, Anant R.Kardi and Carola Schulzke, Kurnada-Corriu Cross-Couplings with 2-Pyridyl Grignard Reagents, Chemistry—A European Journal, Mar. 15, 2010, pp. 3300-3303, vol. 16, No. 11, Wiley-VCH Verlag GmbH & Co. KGaA, Weinheim, DOI: 10.1002/chem.201000032.

Paul R.Parry, Changsheng Wang, Andrei S.Batsanov, Martin R. Bryce and Brian Tarbit, Functionalized Pyridylboronic Acids and Their Suzuki Cross-Coupling Reactions to Yield Novel Heteroarylpyridines, Journal of Organic Chemistry, Sep. 21, 2002, pp. 7541-7543, vol. 67 No. 21, American Chemical Society.

Pubchem Compound—CID 15975233—Compound Summary, Mar. 14, 2007.

*Primary Examiner* — Heidi Reese
(74) *Attorney, Agent, or Firm* — Robert E. Alderson, Jr.

(57) ABSTRACT

Methods for the synthesis of 2-alkoxy-5-(pyridin-2-yl)pyridine of formula I

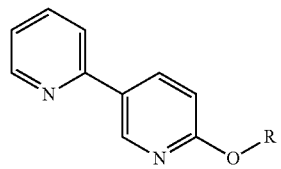

or salts thereof are provided.

13 Claims, No Drawings

METHODS FOR PREPARING INTERMEDIATES OF PERAMPANEL

CROSS REFERENCE TO RELATED APPLICATION

This application claims priority to and benefit of Italian Patent Application No. MI2011A001952 filed Oct. 27, 2011, the contents of which are incorporated by reference in their entirety.

FIELD OF THE INVENTION

The present invention relates to a process for synthesising 2-alkoxy-5-(pyridin-2-yl)pyridine which is an intermediate in the synthesis of the active substance Perampenel.

BACKGROUND OF THE INVENTION

Perampanel is a pharmaceutically active agent, currently in clinical phase 3. It can be used to treat Parkinson's disease, epilepsy and multiple sclerosis.

Perampanel, having the following chemical formula

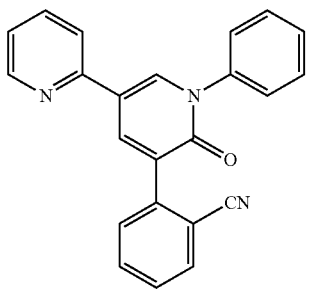 [SMILES: N#Cc1ccccc1-c1cc(-c2ccccn2)cn(-c2ccccc2)c1=O]

is also known as E 2007, ER 155055-90 and 3-(2-cyanophenyl)-1-phenyl-5-(2-pyridil)-1,2-dihydropyridin-2-one Various methods of synthesis of such molecules are known, such as those reported in EP1300396, EP 1465626, EP 1772450, EP 1764361 and EP 1970370.

Many of the methods of synthesis of such active substances reported by the prior art use the key intermediate 5-(2-pyridil)-1,2-dihydropyridin-2-one also known as 2,3'-bipyridin-6'(1'H)-one having the following chemical formula:

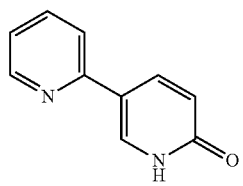 [SMILES: O=c1ccc(-c2ccccn2)c[nH]1]

Other methods use the synthetic precursor of this intermediate known as 2-methoxy-5-(pyridin-2-yl)pyridine or 6'-methoxy-2,3'-bipyridine having the formula:

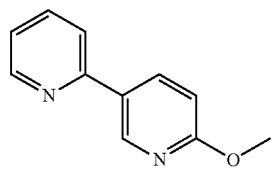

2,3'-bipyridin-6'(1'H)-one. it is in fact prepared by simple acid-catalysed demethylation of the 6'-methoxy-2,3'-bipyridine as is reported in the prior art.

Various ways of synthesising 2-methoxy-5-(pyridin-2-yl) pyridine are known. The process summarised in Diagram (I) below is described in WO 2001096308:

Diagram (I)

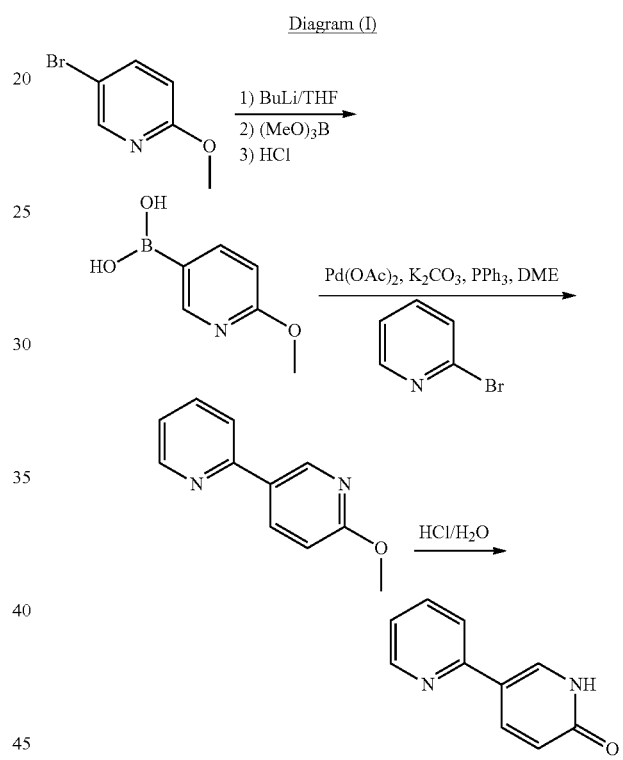

Such process highlights clear disadvantages such as the need to operate in cryogenic conditions (T=−78° C.) using special equipment and the need to isolate boronic acid via work-up. In addition the use of 2-Bromopyridine is required, which exacerbates the production of waste compared to 2-chloropyridine.

Another process described in WO 2004009553 is summarised in Diagram (II):

Daigram (II)

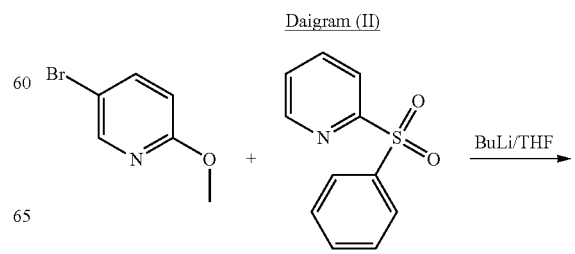

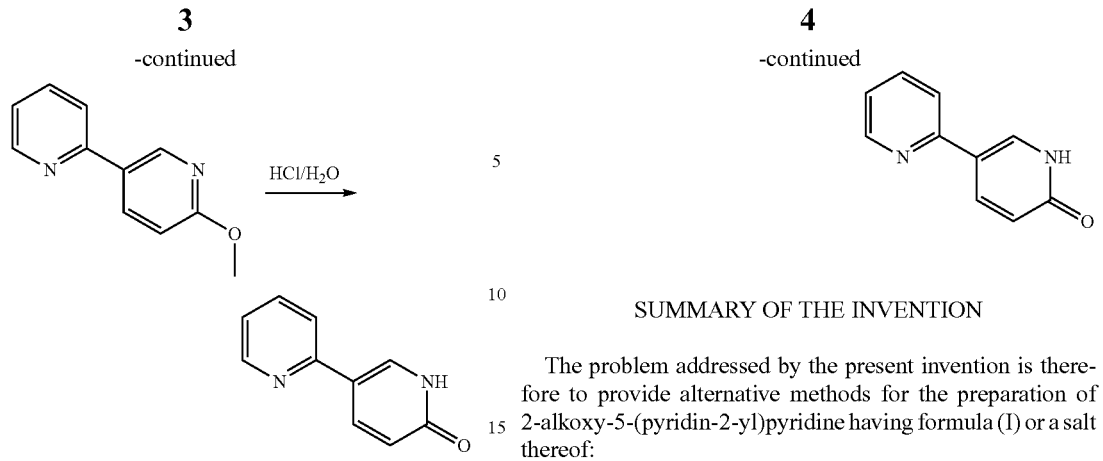

Disadvantages of this process include the use of high molecular weight benzene-sulfonyl pyridine entailing a scarce atom-economy of the process and the need to operate at low temperature T (−78° C.) using special equipment.

Lastly, a completely different process is described in WO20087093392 for the preparation of 2,3'-bipyridin-6'(1'H)-one (Diagram (III)) which however does not include the preparation of the intermediate precursor 2-methoxy-5-(pyridin-2-yl)pyridine:

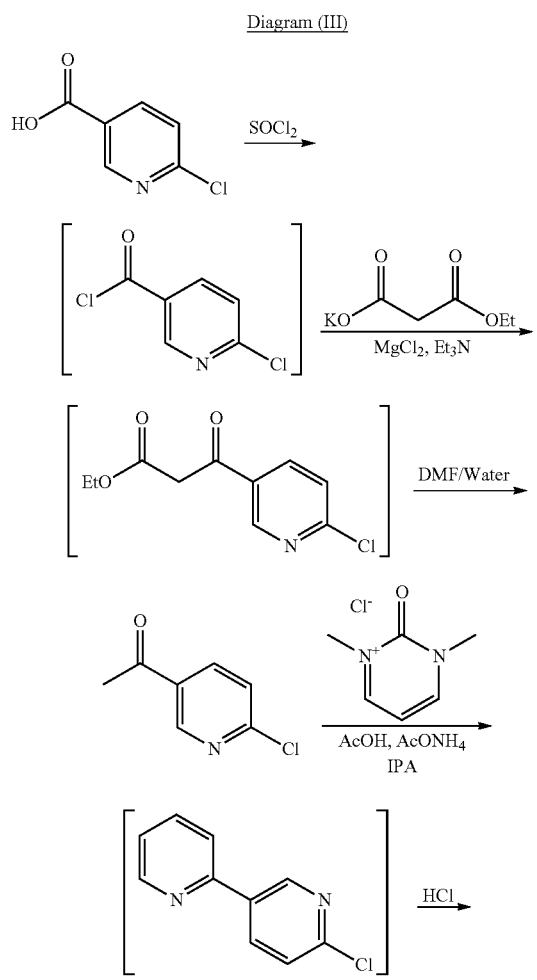

SUMMARY OF THE INVENTION

The problem addressed by the present invention is therefore to provide alternative methods for the preparation of 2-alkoxy-5-(pyridin-2-yl)pyridine having formula (I) or a salt thereof:

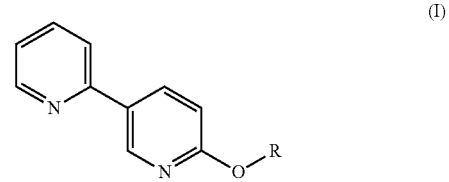

(I)

wherein R is a linear or branched C1-C6 alkyl group, making it possible to overcome at least partially the drawbacks mentioned above with reference to the prior art.

Such problem is resolved by methods for the synthesis of 2-alkoxy-5-(pyridin-2-yl)pyridine of formula (I) or of a salt thereof as delineated in the attached claims.

Further characteristics and advantages of the process according to the invention will be evident from the description below of particular embodiments, made by way of non-limiting examples.

DETAILED DESCRIPTION

The present invention relates to methods for the preparation of 2-alkoxy-5-(pyridin-2-yl)pyridine of formula (I) or salts thereof:

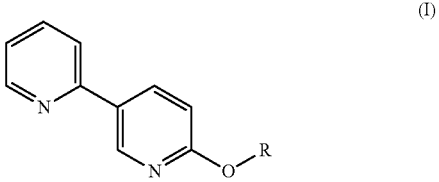

(I)

wherein R is a linear or branched C1-C6 alkyl group, In one embodiment such methods include the following steps:

(a) converting of a 5-halogen-2-alkoxypyridine of formula (IV)

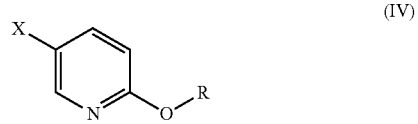

(IV)

in which X is chlorine, bromine or iodine and R is a linear or ramified C1-C6 alkyl group, into a halide of (6-alkoxypyridin-3-yl)magnesium of formula (III) or in a lithium chloride complex thereof having the formula (III-bis):

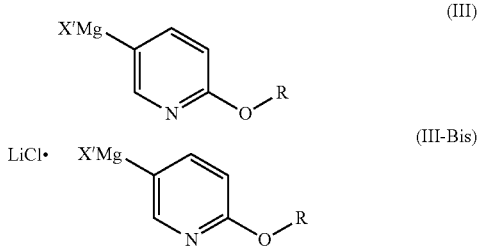

in which X' is chlorine, bromine or iodine, (b) reacting the compound obtained in the step (a) with a 2-halogenpyridine or 2-pseudohalogenpyridine of formula (II)

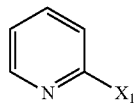

in which $X_1$ is chlorine, bromine, iodine, triflate, nonaflate, mesylate, tosylate or besylate or —O(C=O)NR'$_2$ wherein R' is a linear or branched $C_1$-$C_4$ alkyl group or is phenyl or benzyl, to provide the compound of formula (I) or a salt thereof.

The group R is a linear or branched C1-C6 alkyl group and may be methyl, ethyl, n-propyl, isopropyl, n-butyl, sec-butyl, tert-butyl, n-pentyl, sec-pentyl, isopentyl, neopentyl, n-hexyl, sec-hexyl etc.

In certain embodiments, methods according to the present invention include use of 2-Chloropyridin, as the compound of formula (II) wherein $X_1$ is chlorine.

In other embodiments, methods according to the present invention include use of 2-chloropyridin, as the compound of the formula (II) wherein $X_1$ is chlorine, and use of 5-bromo-2-alkoxypyridine, as the compound of formula (IV) wherein X is bromide.

When the substituent $X_1$ of a compound having the formula (II) is chosen from triflate, nonaflate, mesylate, tosylate and besylate, the bond between such groups and the pyridine ring may utilize an atom of oxygen belonging to the sulphonate group.

When $X_1$ is —O(C=O)NR'$_2$, R' may be a linear or branched $C_1$-$C_4$ alkyl substituent selected, for example, from methyl, ethyl, n-propyl, isopropyl, n-butyl, sec-butyl, tert-butyl, or may be phenyl or benzyl.

Methods according to the present invention and in particular step (b) may be carried out by catalysis performed by a metallic complex of, for example, palladium, nickel, iron or cobalt.

In certain embodiments, step (b) may be performed using as a catalyst a palladium complex having the formula Pd(dppf)Cl$_2$ or solvates thereof, such as Palladium bis-diphenylphosphinoferrocene dichloride or solvates thereof. A typical solvate of this catalyst is that formed with dichloromethane.

The metallic complex used in step (b) may be used in certain embodiments in a molar amount of about 0.1% to about 5%, in other embodiments in molar amount of about 0.1% to about 1% with respect to the compound of formula (II) and in still other embodiments in an amount of about 0.25% mol of catalyst with respect to the compound of formula (II).

Methods according to the present invention include those for which that step (b) may be conducted in an organic solvent chosen from tetrahydrofuran, methyl-tetrahydrofuran, toluene and mixtures thereof.

Moreover, step (b) may be carried out in a temperature range of from about 25 to about 75° C. In certain embodiments this range is between about 45 and about 50° C. between about 25 and about 75° C. step (b) may be completed in a time ranging from about 1 to about 5 hours. At a range from about 45 to about 50° C. the reaction may be completed in about 2 to about 4 hours.

Step (b) may be carried out using from about 1.1 to about 1.7 molar equivalent of a Grignard reagent having the formula (III) or (III-bis) with respect to the 2-halogen pyridine or pseudo halogen pyridine having the formula (II). In certain embodiments about 1.1 to about 1.6 molar equivalent of Grignard reagent may be used and in other embodiments about 1.2 to about 1.5 molar equivalent may be used.

Methods according to the present invention may provide in step (a) the formation of a Grignard reagent having the formula (III) or (III-bis) by means of the reaction between 5-halogen-2-alkoxypyridine having the formula (IV) and a Grignard reagent or a lithium chloride complex thereof or by means of metallic magnesium.

For such purpose, Grignard reagents such as isopropyl magnesium chloride, t-butyl magnesium chloride and relative lithium chloride complexes thereof may be conveniently used as Grignard reagents for the halogen-metal exchange. Isopropyl magnesium chloride and the relative lithium chloride complex thereof are particularly useful.

The Grignard reagent complexes with lithium chloride enable the preparation of intermediates having the formula (III-bis) with greater conversions (99% against 94%), using less reagent and in shorter times than corresponding Grignard reagents without complexes.

If the 5-halogen-2-alkoxypyridine having the formula (IV) has a halogen group X other than a halogen of the Grignard reagent or its lithium chloride complex used for the reaction, the corresponding product having the formula (III) or (III-bis) may have a group X' which could be the same as the starting halogen-2-alkoxypyrdine or alternatively X' could be the halogen of the Grignard reagent used or alternatively a mixture of the compounds with the two different halogens could be obtained. In all such cases the reaction products are understood to be part of the present invention.

The synthesis of Grignard reagents through the use of halogen-metal exchange, i.e. by using another Grignard reagent, according to common general knowledge in the organic chemistry field, is typically conducted at low temperatures, i.e. at temperatures below about 0° C. up to about 20° C.

However, in the present case, it has been unexpectedly found that in step (a) different and more severe conditions are needed to allow the formation of a Grignard reagent having the formula (III) or (III-bis). In particular step (a) should be conducted between about 25° C. and about 70° C. According to certain embodiments step (a) may be carried out at a temperature in the range from about 25 to about 30° C.

In certain embodiments, to prepare a Grignard reagent having the formula (III) or (III-bis) from about 1.3 to about 2.5 and in certain embodiments from about 1.6 to about 2.2 molar equivalents of a Grignard reagent or from about 1.1 to about 1.5 molar equivalents of a Grignard lithium chloride complex reagent, in both cases with respect to the compound of formula (IV), are respectively needed.

The reaction of step (a) may be completed in an interval of time from about 4 to about 72 hours. In particular it may be completed in about 4 to about 15 hours when a Grignard lithium chloride complex reagent is used, while it may be completed in about 15 to about 72 hours when a normal Grignard reagent is used.

In particular embodiments, when performing step (a) at a temperature of about 25 to about 30° C., in which case a Grignard lithium chloride complex reagent in amounts from about 1.1 to about 1.5 molar equivalent, with respect to the compound having the formula (IV), may be used, the reaction may be completed in about 4 to about 8 hours. If about 1.3 to about 1.35 molar equivalent of reagent is used, the reaction may be completed in about 5 hours. The conversion is over about 98%, typically about 99%, measured by HPLC.

When performing step (a) at a temperature of about 25 to about 30° C., in which case a normal Grignard reagent in amounts of approximately 2 molar equivalent may be used, the reaction may be completed in about 24 hours. The conversion is typically on the order of about 94%.

The HPLC (A/A %) purity of the product obtained from step (a) is generally about 94% in all cases, i.e. using either a normal Grignard reagent or a lithium chloride complexes thereof.

The best conditions for carrying out step (a) thus prove to be the use of a Grignard lithium chloride complex reagent in amounts of about 1.3 to about 1.35 molar equivalent with respect to the compound having the formula (IV), operating at a temperature from about 25 to about 30° C. The reaction may be completed in approximately 5 hours. Alternatively, using approximately 2.0 molar equivalent of a normal Grignard reagent, calculated with respect to the compound of formula (IV), and operating at about 25 to about 30° C., the reaction time is approximately 24 hours.

Methods according to the present invention may be used to prepare 2-methoxy-5(pyridine-2-yl)pyridine, i.e. for the compound having the formula (I) wherein R is methyl.

Step (a) according to the present invention therefore allows for the preparation of a halide of (6-alkoxypyridin-3-yl)magnesium of formula (III) or a lithium chloride complex thereof of formula (III-bis):

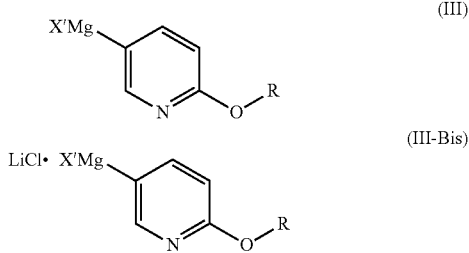

in which X' may be chosen between chlorine, bromine and iodine and R may be a linear or branched C1-C6 alkyl group.

As a result, the compound having the chemical name (6-methoxypyridin-3-yl)magnesium bromide constitutes an intermediate of methods according to the present invention. The compound having the chemical name (6-methoxypyridin-3-yl)magnesium chloride is also an intermediate of the present methods.

The compounds chosen from the group:
a. (6-(C2-C6-alkoxy)pyridin-3-yl)magnesium chloride,
b. (6-(C2-C6-alkoxy)pyridin-3-yl)magnesium bromide,
c. (6-(C1-C6-alkoxy)pyridin-3-yl)magnesium iodide,
d. (6-(C1-C6-alkoxy)pyridin-3-yl)magnesium chloride lithium chloride complex,
e. (6-(C1-C6-alkoxy)pyridin-3-yl)magnesium bromide lithium chloride complex,
f. (6-(C1-C6-alkoxy)pyridin-3-yl)magnesium iodide lithium chloride complex;
also constitute intermediates of methods according to the present invention.

As already explained, a Grignard lithium chloride complex compounds chosen from the group:
a. (6-(C1-C6-alkoxy)pyridin-3-yl)magnesium chloride lithium chloride complex,
b. (6-(C1-C6-alkoxy)pyridin-3-yl)magnesium bromide lithium chloride complex,
c. (6-(C1-C6-alkoxy)pyridin-3-yl)magnesium iodide lithium chloride complex;
are particularly useful.

Among the compounds belonging to the two groups listed above, the compound in which the C1-C6-alkoxy group is a methoxy group is especially useful.

In certain embodiments such synthetic intermediates, prepared by conversion of a 5-halogen-2-(C1-C6-alkoxy)pyridine of formula (IV), which have formula (III) or formula (III-bis), are useful for the preparation of 2-alkoxy-5-(pyridin-2-yl)pyridine of formula (I) in which R is a linear or branched C1-C6 alkyl group or for the preparation of a salt thereof.

The conversion of the step (b) is typically over about 99% and the HPLC (A/A %) purity of the product obtained at the end of the reaction is generally around 94%.

Methods according to the present invention, while considering the yields of step (a) and of step (b), allow for the preparation of the compound of formula (I), at the end of the work-up, with molar yields of about 89 to about 92%.

It is not believed that methods permitting the product (I) to be obtained in similar yields by means of such a simple and economically advantageous process are presently known.

Another advantage provided by methods according to the present invention is that the formation of the Grignard reagent (step (a)), as well as the coupling step (b) between the Grignard reagent and the 2-halogen-pyridine, are carried out at least 25° C. Since it is no longer necessary to isolate the intermediate Grignard reagent, it is possible to perform the entire process in one-pot, even while operating at the same constant temperature, for example, between about 45 and about 50° C.

Methods according to the present invention makes it possible to avoid the use of special cryogenic equipments and having to work at inconvenient temperatures (e.g. −78° C.) as in the previously described processes.

Moreover, since the leaving groups include halogen atoms, methods according to the present invention have a high yield in terms of atom-economy in that the use of "large" leaving groups such as the benzene sulphonates, used in the processes of the prior art, can be avoided.

The compound of formula (I) obtained by methods according to the present invention optionally may be isolated according to the known techniques of organic synthesis and/or subjected directly to acid hydrolysis to form the key intermediate 5-(2-pyridil)-1,2-dihydropyridin-2-one also known as 2,3'-bipyridin-6'(1'H)-one.

In particular the compound 2-alkoxy-5-(pyridin-2-yl)pyridine of formula (I) or a salt thereof:

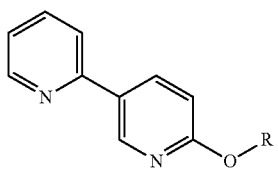

(I)

wherein R is a linear or branched C2-C6 alkyl group in which R may be chosen from ethyl, n-propyl, isopropyl, n-butyl, sec-butyl, tert-butyl, n-pentyl, sec-pentyl, isopentyl, neopentyl, n-hexyl, sec-hexyl, etc. has also been shown to be useful for the preparation of 2,3'-bipyridin-6'(1'H)-one and thereby, ultimately, for the preparation of Permapanel.

For such purposes the compounds of formula (I) wherein R may be an ethyl or isopropyl, even more preferably wherein R is ethyl, may be used.

Surprisingly, the overall molar yield of methods according to the present invention carried out one-pot from the step of hydrolysis of the compound of formula (I) to provide the compound 2,3'-bipyridin-6'(1'H)-one in isolated solid form is typically about 81% starting from the compound of formula (II). It is estimated therefore that the step of hydrolysis of the compound of formula (I) and of isolation of the product 2,3'-bipyridin-6'(1'H)-one has a molar yield of approximately 90%. The product 2,3'-bipyridin-6'(1'H)-one thus obtained has a HPLC purity of over about 99.0% (HPLC A/A %), typically about 99.5%.

EXAMPLES

Example 1

Synthesis of 2-methoxy-5-(pyridin-2-yl)pyridine of formula (I)

Scheme of synthesis

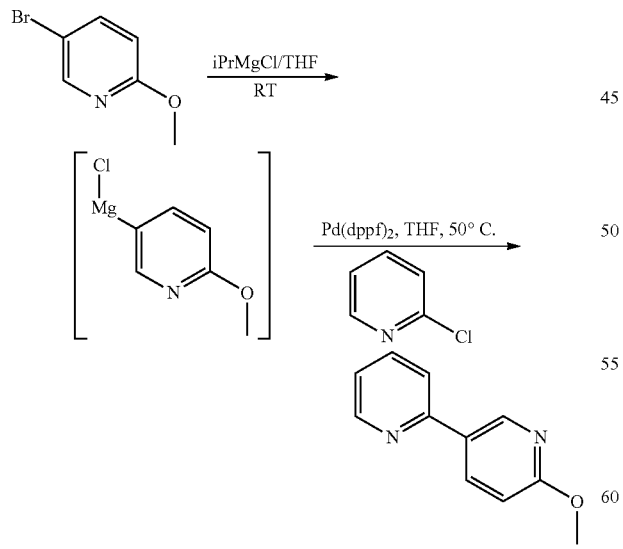

5.0 g of 5-bromo-2-methoxypyridine (1.2 equiv.), 15 ml (6 vol., with respect to 2-chloro pyridine) of anhydrous tetrahydrofuran, previously degassed for 1 hour by bubbling nitrogen through it, were put in a flask previously dried and kept under a nitrogen flow, fitted with a thermometer, a condenser and a dripper funnel. While maintaining the temperature at 25-30° C., 26.6 ml (25.3 g, 1.56 equiv.) of isopropyl magnesium chloride lithium chloride complex 1.3 M in THF were added in about 1 h. The reaction medium was stirred at 25-30° C. for at least 5 h. The conversion, checked via HPLC, was over 95%. 162 mg (1 mol %) of Pd(dppf)Cl$_2$ (1,1'-[bis(diphenylphosphino)ferrocene]dichloropalladium (II)), 2.52 g (1 equiv.) of 2-chloropyridine and 15 ml (6 vol) of previously degassed anhydrous tetrahydrofuran were loaded in another flask previously dried and kept under a nitrogen flow. The reaction medium was heated to 45-50° C. and stirred for 15 min. The suspension of Grignard reagent previously prepared was transferred via a cannula into a suitable dripper funnel. The Grignard reagent was dosed in about 1 h into the flask containing 2-chloropyridine and the catalyser keeping the temperature at 45-50° C. The reaction medium was stirred at 45-50° C. for at least 1 h. The conversion was checked via HPLC. 30 ml (12 vol.) of deionised water were carefully added over a period of 30 min, keeping the temperature at 20-25° C. It was stirred for 15 min., decanted and the phases were separated. The aqueous phase was extracted with two portions of 10 ml (4 vol.) of tert-butyl-methyl ether. The organic phases were combined, dried on anhydrous sodium sulphate and evaporated under a vacuum at T<40° C., to obtain 4.6 g of wet product as a yellow oil having a wt/wt titre of 81.56%, LCAP 78.81%, equal to a molar yield of 90.7%. The raw product was used directly in the next stage of hydrolysis according to the methods of the prior art. 1H-NMR (400 MHz, CDCl$_3$): δ=8.77 (d, J=2.4 Hz, 1H), 8.70-8.69 (m, 1H), 8.28 (dd, J=8.6, 2.5 Hz, 1H), 7.77 (m, 1H), 7.68 (d, J=8.0 Hz, 1H), 7.30-7.23 (m, 1H), 6.87 (d, J=8.7 Hz, 1H), 4.02 (s, 3H). The spectral data are in line with those shown in literature.

Example 2

Synthesis of 2-methoxy-5-(pyridin-2-yl)pyridine of formula (I)

Scheme of synthesis

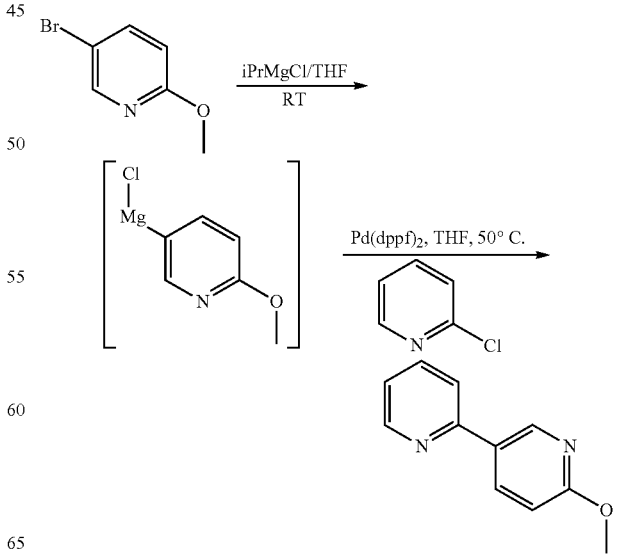

5.0 g of 5-bromo-2-methoxypyridine (1.1 equiv.), 16.5 ml (6 vol with respect to 2-chloro pyridine) of anhydrous tetrahydrofuran, previously degassed for 1 hour by bubbling nitrogen through it, were loaded in a flask previously dried and kept under a nitrogen flow, fitted with a thermometer, a condenser and a dripper funnel. While maintaining the temperature at 25-30° C., 26.6 ml (25.3 g, 1.56 equiv.) of isopropyl magnesium chloride lithium chloride complex 1.3 M in THF were added in about 1 h. It was stirred at 25-30° C. for at least 5 h. The conversion, checked via HPLC, was over 95%. 177 mg (1 mol %) of Pd(dppf)Cl$_2$ (1,1'-[bis(diphenylphosphino)ferrocene]dichloropalladium (II)), 2.74 g (1 equiv.) of 2-chloropyridine and 16.5 ml (6 vol) of previously degassed anhydrous tetrahydrofuran were loaded in another flask previously dried and kept under a nitrogen flow. The reaction medium was heated to 45-50° C. and stirred for 15 min. The suspension of Grignard reagent previously prepared was transferred via a cannula into a suitable dripper funnel. The Grignard reagent was dosed in about 1 h into the flask containing 2-chloropyridine and the catalyser, while keeping the temperature at 45-50° C. It was stirred at 45-50° C. for at least 1 hr. The conversion was checked via HPLC. 33 ml (12 vol.) of deionised water were carefully added, while keeping the temperature at 20-25° C., over a period of 30 min. It was stirred for 15 min., decanted and the phases were separated. The aqueous phase was extracted with two portions of 11 ml (4 vol.) of tert-butyl-methyl ether. The organic phases were washed with 11 ml (4 vol.) of sodium chloride saturate solution. The organic phases were combined, dried on anhydrous sodium sulphate and evaporated under a vacuum at T<40° C., to obtain 3.1 g of wet product as a yellow oil having a wt/wt titre of 82.37%, LCAP 79.35%, equal to a molar yield of 56.8%. (In this experiment there was an accidental loss of product during the separation into phases).

The raw product was used directly in the next stage of hydrolysis according to the methods of the prior art. 1H-NMR (400 MHz, CDCl$_3$): δ=8.77 (d, J=2.4 Hz, 1H), 8.70-8.69 (m, 1H), 8.28 (dd, J=8.6, 2.5 Hz, 1H), 7.77 (m, 1H), 7.68 (d, J=8.0 Hz, 1H), 7.30-7.23 (m, 1H), 6.87 (d, J=8.7 Hz, 1H), 4.02 (s, 3H). The spectral data are in line with those shown in literature.

Example 3

Synthesis of 2-methoxy-5-(pyridin-2-yl)pyridine of formula (I)

Scheme of synthesis

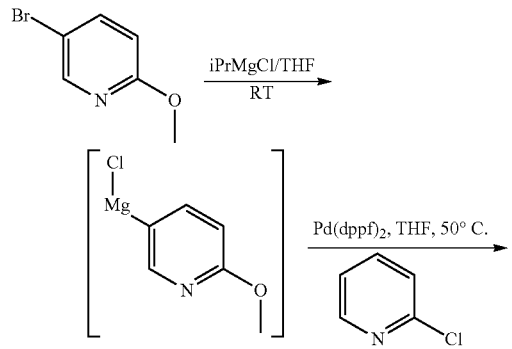

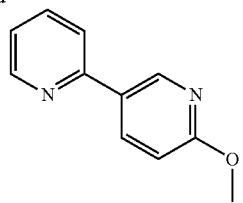

1.09 kg=0.75 L (1.1 equiv., d=1.453 g/ml) of 5-bromo-2-methoxy pyridine and 3.60 L (6 V) of anhydrous toluene, previously degassed under a nitrogen flow, were loaded into a reactor A previously dried under nitrogen. The mixture was heated to 25-30° C. and added with 5.70 kg (1.485 equiv.) of a solution of Isopropyl magnesium chloride lithium chloride complex (20% wt/wt) in THF over about 1 h. It was stirred at 25-30° C. for at least 8 hours (the reaction may be conducted overnight). The conversion was monitored via HPLC. When the reaction was complete, a mixture of 9.67 g of Pd(dppf)Cl2 (0.25 mol %), 0.60 kg equal to 0.50 l (1 equiv., d=1.2 g/ml) of 2-chloropyridine and 3.60 l (6 V) of anhydrous toluene, previously degassed under a nitrogen flow, was loaded into a reactor B, previously dried and kept under a flow of nitrogen. The mixture was stirred at 45-50° C. for 30 min. The suspension of Grignard reagent from reactor A was transferred into reactor B over approximately 1 hr, while keeping the T at 45-50° C. Upon completion, stirring was prosecuted for at least 4 hr at 45-50° C. The conversion was monitored in HPLC (>99%; HPLC purity A/A % of the product >94%). When the reaction was complete, the mixture was cooled to 25-30° C., added with 3.60 L (6 V) of purified water carefully, keeping the temperature at 20-25° C., over about 30 min.-1 hr. Stirring was prosecuted for 15 min. The biphasic mixture was filtered on paper and the solid residue was washed with 0.60 L (1 V) of toluene. The filtrate was loaded into the reactor C. The organic phase (containing the reaction product) was separated. 3.60 L (6 V) of purified water were added to the organic phase. Stirring was continued for 15 min, the mixture was left to decant and the phases were separated. The organic phase (containing the reaction product) was recovered. A solution of Hydrochloric acid 4 M, prepared by using 1.41 L (2.35 V) of concentrated hydrochloric acid and 2.06 L (3.44V) of purified water, was added to the organic phase. Stirring was continued for 15 min, the mixture was left to decant and the aqueous acid phase (the product was in aqueous phase) was separated. The acid aqueous phase (containing the product) was washed twice with 1.20 L (2×2V) of MTBE. The aqueous phase was separated and weighed. Determination of the yield in solution of 2-methoxy-5-(pyridine-2-yl)pyridine was made by external standard HPLC analysis (molar yield in solution: 90.3%):

Example 4

Synthesis of 5-(2-pyridil)-1,2-dihydropyridin-2-one or 2,3'-bipyridin-6'(1'H)-one The acid aqueous phase containing 2-methoxy-5-(pyridin-2-yl)pyridine obtained according to Example 3 was reintroduced into the reactor C. The mixture was heated to reflux (95-100° C.) for at least 4 h. The conversion was monitored in HPLC. When the reaction was complete, it was cooled to 20-25° C., the acid aqueous phase was washed with 3.54 L (5.9 V) of MTBE (the product was in aqueous phase). Stirring was continued for 15 min, the mixture was left to decant and the phases were separated. Once the phases were separated, the pH of the aqueous phase (containing the product) was adjusted to 12.5-13 with approximately 1.5 L of sodium hydroxide 30% solution. The basic aqueous phase so obtained was washed with 3.54 L (5.9 V) of MTBE (the product was in aqueous phase). Stirring was continued for 15 min, the mixture was left to decant and the phases were separated. The pH of the aqueous phase was adjusted to about 7-7.5 with approximately 0.3 L of concentrated hydrochloric acid. 7.26 L (12.1 V) of n-butanol and a solution of sodium chloride at 20%, obtained by mixing 0.67 kg (1.12 W) of sodium chloride and 2.68 l (4.47 V) of purified water, were added to the aqueous phase. Stirring was continued for 15 min, the mixture was left to decant and the phases were separated (the product passed into the organic phase). The aqueous phase was again extracted with 7.26 L (12.1 V) of n-butanol. Stirring was continued for 15 min, the mixture was left to decant and the phases were separated. The organic phase so obtained were evaporated at 45-60° C. under vacuum to a residue. The distillation residue was recovered with 2.4 L (4 V) of ethyl acetate. The mixture was heated to reflux and stirred for 15 min. It was cooled to 20-25° C. and stirred 30 min and then it was cooled to −10/−5° C. and stirred for at least 2 h. The mixture was filtered and washed with 2×0.60 L (2×1 V) of cold ethyl acetate (−10-5° C.). The product was dried at 45-50° C. under vacuum for at least 6 h. 736 g of product were obtained, equal to a molar yield of 80.9% from starting 2-chloro-pyridine (HPLC purity A/A % 99.4%).

Example 5

Synthesis of 2-Ethoxy-5-(pyridin-2-yl)pyridine of formula (I with R=Et)

Example 3 was repeated, but 5-bromo-2-Ethoxy pyridine (Aldrich) was used in place of 5-bromo-2-methoxy pyridine and it was performed with 5 grams of the starting compound.

2-Ethoxy-5-(pyridin-2-yl)pyridine so obtained has the following spectrum 1H-NMR (400 MHz, CDCl$_3$): δ=8.76 (dd, J=2.5, 0.6 Hz, 1H), 8.71-8.69 (m, 1H), 8.28 (dd, J=8.6, 2.5 Hz, 1H), 7.80-7.75 (m, 1H), 7.68 (dt, J=8.0, 1.0 Hz, 1H), 7.27-7.24 (m, 1H), 6.86 (dd, J=8.7, 0.7 Hz, 1H), 4.46 (q, J=7.1 Hz, 2H), 1.37 (t, J=7.1 Hz, 3H).

Subjecting 2-Ethoxy-5-(pyridin-2-yl)pyridine to the same conditions of hydrolysis as in example 4 so as to obtain 2,3'-bipyridin-6'(1'H)-one, the hydrolysis reaction was already complete in 4 hours at reflux. Such intermediate is very useful for preparing 2,3'-bipyridin-6'(1'H)-one and therefore Perampanel.

Example 6

Synthesis of 2-Isopropoxy-5-(pyridin-2-yl)pyridine having the formula (I with R=iPr)

Example 3 was repeated, but 5-bromo-2-isopropoxy pyridine (Aldrich) was used in place of 5-bromo-2-methoxy pyridine and it was performed with 1 gram of the starting compound.

2-isopropoxy-5-(pyridin-2-yl)pyridine so obtained has the following spectrum 1H-NMR (400 MHz, CDCl$_3$): δ=8.75 (d, J=2.3 Hz, 1H), 8.69-8.68 (m, 1H), 8.25-8.22 (m, 1H), 7.79-7.74 (m, 1H), 7.68 (dt, J=8.0, 0.8 Hz, 1H), 7.26-7.22 (m, 1H), 6.80 (dd, J=8.7, 0.5 Hz, 1H), 5.33 (sept, J=6.2 Hz, 1H), 1.40 (d, J=6.2 Hz, 6H).

Subjecting 2-Isopropoxy-5-(pyridin-2-yl)pyridine to the same conditions of hydrolysis as in example 4 so as to obtain 2,3'-bipyridin-6'(1'H)-one, the hydrolysis reaction was already complete in 4 hours at reflux. Such intermediate is very useful for preparing 2,3'-bipyridin-6'(1'H)-one and therefore Perampanel.

In particular it may be appreciated how methods according to the present invention make it possible to obtain 2-alkoxy-5-(pyridine-2-yl)pyridine of formula (I) or salts thereof, with good yields, excellent atom-economy of the process, in a single step and avoiding the use of cryogenic equipment and conditions.

The invention claimed is:

1. A method for the preparation of 2-alkoxy-5-(pyridin-2-yl)pyridine of formula (I) or of a salt thereof:

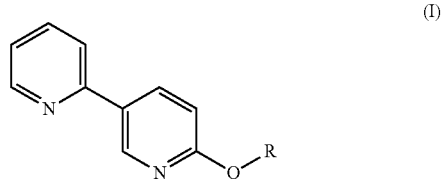

wherein R is a linear or branched C1-C6 alkyl group, comprising the following steps:

(a) converting of a 5-halogen-2-alkoxypyridine of formula (IV)

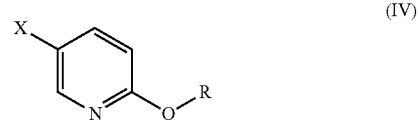

wherein X is selected from the group consisting of: chlorine, bromine and iodine and R is a linear or branched C1-C6 alkyl group, into a halide of (6-alkoxypyridin-3-yl)magnesium of formula (III) or in a lithium chloride complex thereof of formula all-bis):

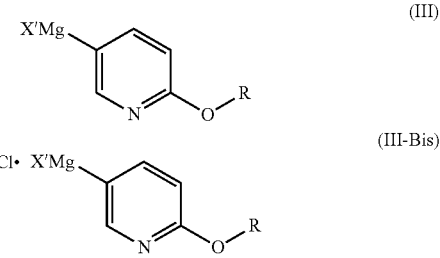

wherein X' is selected from the group consisting of: chlorine, bromine and iodine, (b) reacting of the compound obtained in the step (a) with a 2-halogenpyridine or 2-pseudohalogenpyridine of formula (II)

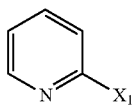 (II)

wherein X' is selected from the group consisting of: chlorine, bromine, iodine, triflate, nonaflate, mesylate, tosylate and besylate or —O(C=O)NR'$_2$ and wherein R' is a linear or branched C$_1$-C$_4$ alkyl group or is phenyl or benzyl, to provide the compound of formula (I) or a salt thereof.

2. The method of claim 1 wherein X$_1$ is chlorine.

3. The method of claim 1 wherein step (b) is catalyzed by a metallic complex comprising an element selected from the group consisting of: of palladium, nickel, iron and cobalt.

4. The method of claim 3 wherein the complex of palladium is Pd(dppf)Cl$_2$ or solvates thereof.

5. The method of claim 3 wherein the metallic complex is used in a molar amount of about 0.1% to about 1% with respect to the compound of formula (II).

6. The method of claim 1, wherein step (b) is carried out in a temperature range from about 25 to about 75° C.

7. The method of claim 6, wherein step (b) is carried out between about 45 and about 50° C.

8. The method of claim 1, wherein step (a) is carried out by means of a Grignard reagent or a Lithium chloride complex thereof or by means of metallic magnesium.

9. The method of claim 8, wherein the Grignard reagent is selected from the group consisting of: Isopropyl magnesium chloride, t-butyl magnesium chloride and their lithium chloride complexes.

10. The method of claim 1 wherein step (a) is carried out between about 25° C. and about 70° C.

11. The method of claim 10, wherein step (a) is carried out between about 25 and about 30° C.

12. The method of claim 1, wherein step (a) is carried out using about 1.3 to about 2.5 molar equivalents of a Grignard reagent or by about 1.1 to about 1.5 molar equivalents of a Grignard reagent lithium chloride complex, in both cases with respect to the compound of formula (IV).

13. The method of claim 1 wherein R is methyl.

* * * * *